(12) United States Patent
He et al.

(10) Patent No.: US 11,471,223 B2
(45) Date of Patent: Oct. 18, 2022

(54) METHOD FOR POSITIONING AND NAVIGATION OF A FRACTURE CLOSED REDUCTION SURGERY AND POSITIONING DEVICE FOR THE SAME

(71) Applicant: HANGZHOU SANTAN MEDICAL TECHNOLOGY CO., LTD., Zhejiang (CN)

(72) Inventors: Bin He, Zhejiang (CN); Liping Shen, Zhejiang (CN)

(73) Assignee: HANGZHOU SANTAN MEDICAL TECHNOLOGY CO., LTD., Hangzhou (CN)

( * ) Notice: Subject to any disclaimer, the term of this patent is extended or adjusted under 35 U.S.C. 154(b) by 0 days.

(21) Appl. No.: 17/556,982

(22) Filed: Dec. 20, 2021

(65) Prior Publication Data
US 2022/0110697 A1    Apr. 14, 2022

Related U.S. Application Data (63) Continuation of application No. PCT/CN2019/096349, filed on Jul. 17, 2019.

(51) Int. Cl.
*A61B 17/66* (2006.01)
*A61B 34/20* (2016.01)
(Continued)

(52) U.S. Cl.
CPC .............. *A61B 34/20* (2016.02); *A61B 17/66* (2013.01); *A61B 2017/564* (2013.01); *A61B 2034/2072* (2016.02); *A61B 2090/3762* (2016.02)

(58) Field of Classification Search
CPC .... A61B 2034/2046; A61B 2034/2051; A61B 2034/2055; A61B 17/58–60;
(Continued)

(56) References Cited

U.S. PATENT DOCUMENTS 6,241,735 B1 * 6/2001 Marmulla .............. A61B 34/20
606/130
2003/0004518 A1 * 1/2003 Perren ................ A61B 17/6483
606/102
(Continued)

FOREIGN PATENT DOCUMENTS

CN        104055520 A    9/2014
CN        105361950 A    3/2016
(Continued)

OTHER PUBLICATIONS

International Search Report of PCT/CN2019/096349.
Written Opinion of PCT/CN2019/096349.

*Primary Examiner* — Eduardo C Robert
*Assistant Examiner* — Michelle C Eckman
(74) *Attorney, Agent, or Firm* — Dragon Sun Law Firm, PC; Jinggao Li; Nathaniel Perkins (57) ABSTRACT

The present invention relates to a method for positioning and navigation of a fracture closed reduction surgery, comprising: installing preoperative positioning devices (1), performing CT-scanning to obtain image information of broken bones and the preoperative positioning devices; determining data information of broken bone segments and of positioning balls of the preoperative positioning devices(1); taking a broken bone segment and a preoperative positioning device (1) as a group to divide the obtained data information into data groups, determining ball center coordinates of the positioning balls (9); determining a matching relation between each preoperative positioning device (1) and the corresponding broken bone segment based on the ball center coordinates of the positioning balls(9); detaching the preoperative positioning devices(1), and installing intraoperative positioning devices (11); identifying indicator balls (14) of the intraoperative positioning devices (11) using infrared
(Continued)

light tracking to determine ball center coordinates of the indicator balls in each intraoperative positioning device(11).

17 Claims, 6 Drawing Sheets

(51) Int. Cl.
*A61B 90/00* (2016.01)
*A61B 17/56* (2006.01)

(58) Field of Classification Search
CPC ............... A61B 17/64; A61B 17/6416; A61B 17/6441–66; A61B 2017/564; A61B 34/20
See application file for complete search history.

(56) References Cited

U.S. PATENT DOCUMENTS

| | | | | |
|---|---|---|---|---|
| 2003/0078565 A1* | 4/2003 | Vilsmeier | ............. | F16B 35/041 606/1 |
| 2005/0109855 A1* | 5/2005 | McCombs | ............. | A61B 90/36 236/100 |
| 2005/0197569 A1* | 9/2005 | McCombs | ............. | A61B 34/20 600/426 |
| 2005/0203384 A1* | 9/2005 | Sati | ............. | G06F 3/017 600/426 |
| 2005/0279368 A1* | 12/2005 | McCombs | ............. | A61B 90/36 606/1 |
| 2006/0015018 A1* | 1/2006 | Jutras | ............. | A61B 34/20 600/301 |
| 2006/0241388 A1* | 10/2006 | Lavallee | ............. | A61B 34/20 600/416 |
| 2007/0016009 A1* | 1/2007 | Lakin | ............. | A61B 90/39 600/424 |
| 2008/0077052 A1* | 3/2008 | Tuma | ............. | A61B 34/20 600/587 |
| 2008/0154125 A1* | 6/2008 | Maier | ............. | G16Z 99/00 600/424 |
| 2014/0049629 A1* | 2/2014 | Siewerdsen | ............. | A61B 34/20 348/77 |
| 2015/0031985 A1* | 1/2015 | Reddy | ............. | A61B 34/20 600/424 |
| 2018/0310900 A1 | 11/2018 | Garlow et al. | | |
| 2020/0170751 A1* | 6/2020 | Pack | ............. | A61B 34/30 |
| 2021/0369353 A1* | 12/2021 | Nikou | ............. | A61B 34/30 |

FOREIGN PATENT DOCUMENTS

| | | | |
|---|---|---|---|
| CN | 107182200 A | 9/2017 | |
| CN | 107440797 A | 12/2017 | |
| CN | 107468351 A | 12/2017 | |
| CN | 107874832 A | 4/2018 | |
| CN | 108210073 A | 6/2018 | |
| CN | 108969100 A | 12/2018 | |
| CN | 109009436 A | 12/2018 | |
| WO | WO-2019090705 A1 * | 5/2019 | ............. A61B 34/20 |

\* cited by examiner

METHOD FOR POSITIONING AND NAVIGATION OF A FRACTURE CLOSED REDUCTION SURGERY AND POSITIONING DEVICE FOR THE SAME

CROSS-REFERENCE TO RELATED APPLICATION

This application is a bypass continuation application of PCT application no.: PCT/CN2019/096349. This application claims priority from PCT Application No. PCT/CN2019/096349, filed Jul. 17, 2019, the contents of which is incorporated herein in the entirety by reference.

TECHNICAL FIELD OF THE INVENTION

The present invention relates to a method for positioning and navigation of a fracture closed reduction surgery, and in particularly, to positioning and navigation for a closed reduction surgery of broken bones or fractures, and a positioning device for the navigation method.

BACKGROUND OF THE DISCLOSURE

In existing interventional surgeries, surgical operation is normally unnecessary, it is only required for a specially-made surgical equipment to reach a human lesion location or a surgical target location from a very small wound, then achieving a therapeutic purposes via various of physical or chemical therapies. During the interventional surgery, medical staff cannot visually see, with naked eyes, a lesion or a part to be treated within the patient's body, so that a computer assisted surgery navigation technique is generated. A surgery navigation system associates preoperative medical image information of the patient with a surgical portion in the surgery by means of a positioning device, and finally projecting an image or a three-dimensional image of the lesion or surgical portion to a screen, so as to help medical staff to perform the surgery. As performing a surgery to a human organ or body part, although the preoperative medical image is interrelated with the surgical portion in the surgery via the positioning device, the positioning device does not directly fixed over the lesion.

For a patient with a fracture, it is necessary to reposition the broken bones via surgery, and then closing the repositioned bones with each other. Human skeleton is wrapped with muscle and skin, such that the doctor treating the broken bones or fracture cannot directly see or observe, with naked eyes, the position, pose, displacement and etc. of the broken bones. Hence, a computer assisted surgery navigation system is also adopted in the closed reduction surgery for broken bones or fractures, helping medical staff to better obtain the situation of the injured limb and to know about the position of the broken bone in order to perform the surgery.

In the prior art, CT or X-ray is normally used to obtain a state of patient's skeleton before and during surgical operation. Using X-ray fluoroscopy or CT-scanning to provide a shape, a position and other information of the broken bones, radiation damage is present for both of the patient and the medical staff during the surgery.

DISCLOSURE OF THE INVENTION

In order to solve the above problem present in the prior art, the present invention provides a fracture closed reduction surgery navigation method for precisely displaying a state of fracture or broken bones during a surgery without using X-ray fluoroscopy or CT-scanning and a positioning device for implementing the method.

In order to achieve the purpose of the present invention, the present invention provides a method for positioning and navigation of a fracture closed reduction surgery, comprising:

installing preoperative positioning devices on steel needles of an external fixator, performing CT-scanning to obtain image information of broken bones and the preoperative positioning devices;

determining data information of broken bone segments and of positioning balls of the preoperative positioning devices; taking a broken bone segment and a preoperative positioning device as a group to divide the obtained data information into data groups, determining ball center coordinates of the positioning balls of the preoperative positioning device included in each data group, and determining a distribution rule of the positioning balls according to the ball center coordinates;

determining a matching relation between each preoperative positioning device and the corresponding broken bone segment based on the ball center coordinates of the positioning balls;

detaching preoperative positioning indicators and preoperative positioning support rods in the preoperative positioning devices, and installing intraoperative positioning indicators and intraoperative positioning support rods on the same positioning seat;

identifying indicator balls of the intraoperative positioning devices using infrared light tracking to determine ball center coordinates of the indicator balls in each intraoperative positioning device;

determining spatial pose of the intraoperative positioning devices according to the ball center coordinates of each intraoperative positioning device, and determining spatial pose of each broken bone segment during the surgery according to the coordinate transformation relationship between the preoperative positioning devices and the intraoperative positioning devices; and rendering and displaying the each broken bone segment in real time.

According to an aspect of the present invention, one preoperative positioning device is provided at least on each broken bone segment.

According to an aspect of the present invention, the preoperative positioning device and intraoperative positioning device respectively comprise an support rod and a positioning indicator used before and during the surgery, and an identical, shared positioning seat, wherein the positioning indicator comprises positioning balls; the spatial positions of and the distance between the positioning balls for the preoperative and between the positioning balls for the intraoperative positioning device are the same; the positioning support rod of the preoperative positioning device has a length less than that of the intraoperative support rod.

According to an aspect of the present invention, the positioning balls of the preoperative positioning device are metallic balls, the positioning balls of the intraoperative positioning device are plastic balls coated with an infrared reflection layer on their surfaces.

According to an aspect of the present invention, the positioning balls which are corresponding to each other in the preoperative and intraoperative positioning devices have the same spatial position and distribution rule, and respectively have a respective Z-coordinate in the same three-dimensional coordinate system. That is to say, the preoperative positioning support rod has a length less than that of the intraoperative positioning support rod, so that the group of positioning balls in the preoperative positioning device has the same spatial position with respect to each positioning ball in the intraoperative positioning device, but at a different height, that is, expect for the Z-coordinate, the rest of coordinates of the both are the same in the same three-dimensional coordinate system.

For achieving the purpose of the present invention, the present invention further provides a positioning device for fracture closed reduction, comprising: a positioning seat, a positioning indicator, a preoperative positioning support rod or a intraoperative positioning support rod, the preoperative positioning support rod or intraoperative positioning support rod being connected to the positioning indicator at one end, and detachably affixed and connected to the positioning seat at the other end, wherein the preoperative positioning support rod has a length less than that of the intraoperative positioning support rod.

According to an aspect of the present invention, the ratio of length between the preoperative positioning support rod (4) and the intraoperative positioning support rod (13) is 1:5, in particular, the length of the preoperative positioning support rod (4) is 20 mm, and the length of the intraoperative positioning support rod (13) is 100 mm.

According an aspect of the present invention, the positioning indicator comprises the preoperative positioning indicator and the intraoperative positioning indicator, the preoperative positioning indicator includes preoperative positioning balls which are metal balls, and the intraoperative positioning indicator includes positioning balls which are plastic balls coated with an infrared reflection layer on the outer surface thereof; the spatial distance between ball centers in the preoperative positioning balls is as same as that in the intraoperative positioning balls.

According to an aspect of the present invention, the positioning seat comprises a steel needle holder and a positioning support rod seat, the steel needle holder being rigidly connected to the positioning support rod seat.

According to an aspect of the present invention, the steel needle holder comprises a notch disposed on one end, behind the notch two half-rounded grooves that face each other are provided in the direction extending from the notch towards the interior of the steel needle holder, behind the half-rounded grooves there is provided two opposing protrusions on which a screw is provided, and behind the protrusions a connecting band is provided to elastically connect the two protrusions (20 to each other.

According to an aspect of the present invention, steel needle holder comprises a circular through hole, behind which two protrusions that face each other are provided in the direction extending towards the interior of the steel needle holder, a screw is provided on the protrusions, and behind the protrusions a connecting band is provided to elastically connect the two protrusions to each other.

According to an aspect of the present invention, the positioning support rod seat is provided with a through groove which is provided with a screw on a lateral side.

According to an aspect of the present invention, the through groove has a rectangular, circular or hexagonal cross section.

According to an aspect of the present invention, the through groove is a dovetail groove having an included angle θ of 30°-80°, in particular 60°, there is provided a bead screw on the side wall of the through groove, and the cross section of the preoperative positioning support rod or the intraoperative positioning support rod is trapezoid which matches with the shape of the dovetail groove.

According to an aspect of the present invention, the through groove is provided with a misplug-proof groove on the side wall, and a misplug-proof protrusion corresponding to the misplug-proof groove on the side wall of the through groove is provided on a surface of the preoperative positioning support rod or the intraoperative positioning support rod.

According to an aspect of the present invention, indicator color spots which are corresponding to each other are respectively provided on the steel needle holder and the preoperative positioning support rod and/or intraoperative positioning support rod.

According to the present invention, a positioning support rod with a different length is used respectively in the preoperative positioning device and the intraoperative positioning device, the preoperative positioning support rod is short, while the intraoperative positioning support rod is relatively long. During the preoperative scanning, due to the short preoperative positioning support rod, the preoperative positioning indicator is disposed near the injured limb, keeping away from the external fixator, such that the external fixator which has mounted on the injured limb cannot affect the CT or X-ray scanning on the positioning balls in the preoperative positioning device. In the intraoperative positioning device, a longer intraoperative positioning support rod is adopted such that the intraoperative positioning device is mounted at a position further away from the injured limb, exceeding the external fixator in the height and keeping away from the injured limb. Hence, as performing infrared tracking, it can be ensured that the infrared light may irradiate directly on the positioning balls in the intraoperative positioning device, and the tracking will not be ruined due to blocking of positioning balls by the external fixator.

According to the present invention, the same positioning seat is used before and during the surgery, with the positioning seat being mounted on the steel needle inserted in the broken bone segment, so that, other than the distance relative to the broken bone segment, the rest of positional relationships of the preoperative and intraoperative positioning devices relative to the broken bone segment keep unchanged. By means of the preoperative scanning, the position relationship between the positioning balls and the broken bone segments in the preoperative positioning device is determined. During the surgery, the ball center coordinates of positioning balls in the positioning device are determined via infrared tracking. Since the preoperative positioning balls and the intraoperative positioning balls have the same distribution rule in the three-dimensional space, the broken bone segment corresponding to the tracked intraoperative positioning balls is determined by determining the ball center coordinates of the intraoperative positioning balls and making a comparison with the ball center coordinates of the preoperative positioning balls. The position coordinates and pose of the broken bone segments during the surgery can be deducted and obtained by adding a length differential between the preoperative positioning support rod and the intraoperative positioning support rod to the obtained ball center coordinates of the intraoperative positioning balls. It follows that the deviation between the position of the preoperative positioning balls relative to the broken bone segments and the position of the intraoperative positioning balls relative to the broken bone segments is merely the manufacture deviation of components in the preoperative and intraoperative positioning devices. The accuracy of positioning the broken bone segments is thus enhanced enormously, providing surgeons with exact position information of the broken bone segments.

Position of the positioning balls during the surgery is tracked by an infrared tracking apparatus, without determining the broken bone's position by X-ray fluoroscopy or CT-scanning, radiation damage of X-ray to patients and medical staff during the surgery can be therefore completely eradicated.

According to the present invention, the positioning balls are corresponding to and associated with the respective broken bone, so that the related broken bone segment can be determined by the aid of the positioning balls during information processing or calculation. Hence, according to the above invention concept, it is beneficial to the calculation and determination of positional information of different bone segments by capturing the information of all broken bones or broken bone pieces during one CT-scanning or infrared tracking, then determining the related bone segment based on the positioning balls, and further dividing the captured overall information into information of each related bone segment.

According to the present invention, the positioning seat is fixedly connected to the steel needle in the external fixator before and during the surgery, only with different positioning support rod and positioning indicator are replaced according to advancement of the inspection and treatment processes, such that the positioning balls keep fixed with respect to the position of the broken bone segment and therefore the positioning accuracy between the broken bone segment and the positioning device is essentially improved. According to the present invention, there is absolutely no drift and change in position between the broken bone and the positioning device before and during the surgery. This makes the positions and poses of the broken bone segments as well as the relationship between the broken bone segments, which are displayed to the doctors during the surgery, completely coincident with the practical situation.

According to the present invention, a misplug-proof structure is provided in the preoperative and intraoperative positioning devices, which helps a doctor or nurse to quickly, accurately mount the positioning devices during the surgery, effectively preventing positioning error caused by incorrect installation of the intraoperative positioning support rod.

According to the present invention, if coordinate systems are respectively established for the preoperative positioning device and the intraoperative positioning device, the replacement of the preoperative positioning device with the intraoperative positioning device only relate to a translation of the two coordinate systems, because in the preoperative and intraoperative positioning devices, only the length of the positioning support rod is changeable and other structural features are the same. Hence, according to the present invention, the real-time position, pose and other information of the broken bone segments are not determined by CT or X-ray and other methods during the surgery, but deduced by infrared ray and translational transformation relation of the two coordinate systems and then displaying to surgeons. Thus, there is no risk of radiation damage during the surgery according to the present invention.

DESCRIPTION OF THE PREFERRED EMBODIMENTS

Figure 1:
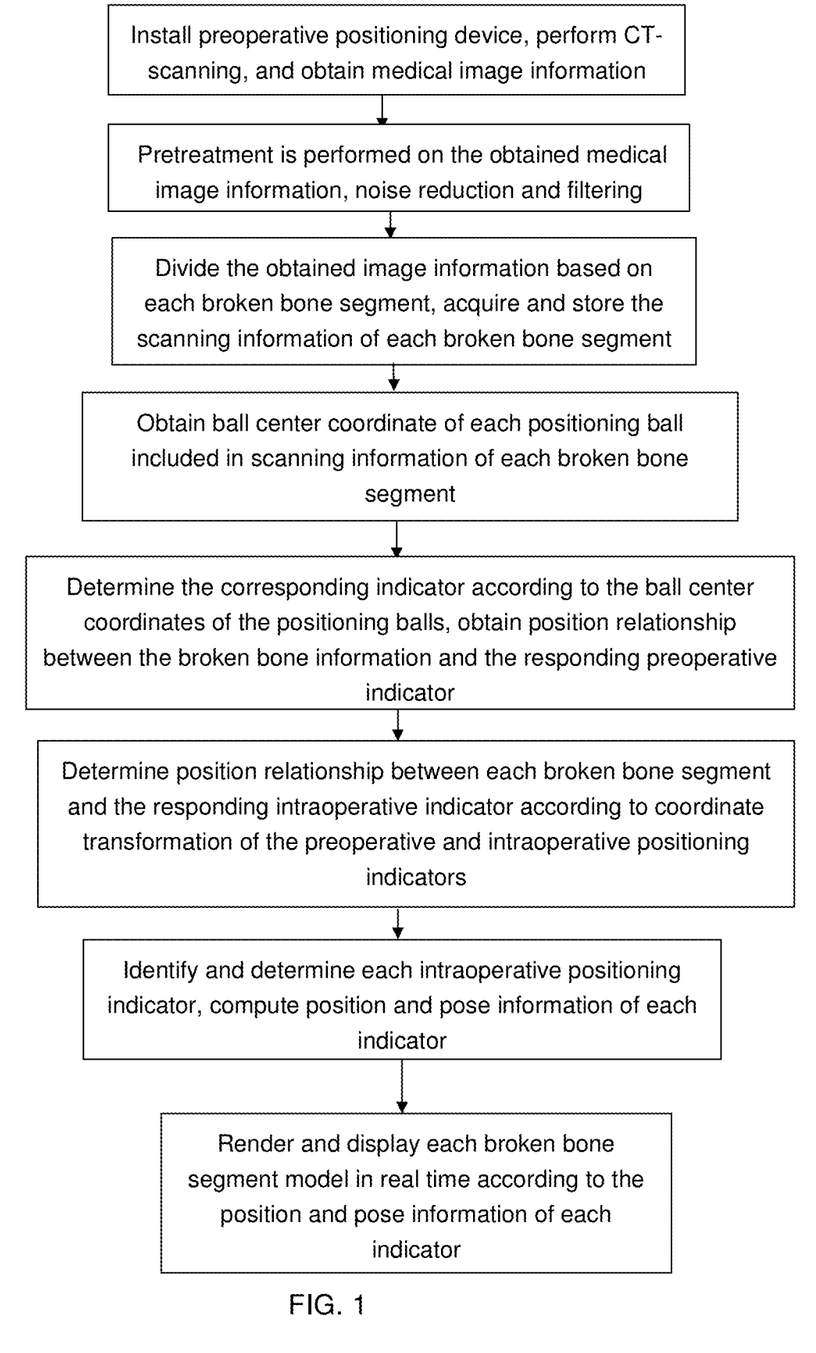
FIG. 1 is a schematic flowchart of the positioning and navigation method for fracture closed reduction surgery according to the present invention.

FIG. 1 is a flowchart schematically showing the positioning and navigation method for fracture closed reduction surgery according to the present invention. The method according to the present invention concept is illustrated in combination with the FIG. 1 below.

Normally, when a patient with fractures reaches hospital, it is firstly needed to affix the broken bones, then performing a closed reduction surgery to the broken bones or fractured bones, such that it is required to mount an external fixator on the injured limb of the patient to affix broken bone segments. Thereafter, CT or X-ray and etc. are used to scan the injured limb which has been affixed by the external fixator and obtaining medical image information of the broken bones. During the surgery, CT or X-ray and etc. are used again to acquire a position, pose information of the broken bones for guiding surgeons to perform the closed reduction surgery.

According to present invention concept, the preoperative positioning device includes a positioning seat, a preoperative positioning support rod and a preoperative positioning indicator. After mounting the external fixator on the injured limb, the positioning seat in accordance with the present invention concept is mounted on and fixedly connected to a steel needle in the external fixator on the injured limb, following which the preoperative positioning support rod and the preoperative positioning indicator are mounted on the positioning seat. The preoperative positioning indicator in the preoperative positioning device comprises positioning balls and a bracket for supporting the positioning balls. The shape and structure of the bracket for supporting the positioning balls mainly serve to keep each positioning ball in a different coordinate position in the same three-dimensional coordinate system. According to the present invention, four positioning balls are used which are disposed at different heights with respect to the horizontal plane and spaced apart from each other, wherein at least three balls are not in the same line. According to the present invention, the distribution rule of the four balls is to distribute them spaced apart from each other at different heights in the three-dimensional coordinate system, with at least three balls are not in the same line. In a word, four balls are not coplanar and three balls are not collinear.

According to the present invention, the positioning indicators in the preoperative positioning devices which are respectively mounted on the broken segments are different from one another. Hence, the positioning balls mounted on each broken bone segment has a different distribution status or a different distribution rule in the three-dimensional space, such that each broken bone segment is corresponding to a unique, specifically paired positioning device. According to the fixation relation or matching relation between the positioning devices and the broken bone segments, a corresponding broken bone segment can be determined by identifying the positioning device. Then, the position coordinates and pose of the corresponding broken bone segment during the surgery can be deduced via a positional relation between the preoperative positioning device and the intraoperative positioning device. As such, the preoperative and intraoperative positioning devices are mounted on the same positioning seat, so that they are located at the same position only with a different height. The resulting intraoperative position images of the broken bone segments are thus highly consistent with the actual broken bone segments without image shift.

According to the present invention, a preoperative broken bone medical image of the injured limb is obtained via a CT-scanning apparatus. Accordingly, the positioning balls of the preoperative positioning device are made of a metallic material. For example, the metal balls are made of aluminum material. This may help to obtain a legible image of the broken bone.

After having mounted the preoperative positioning device, the injured limb is scanned via the CT-apparatus, thereby obtaining medical image information containing all of the broken bone segments and the correspondingly paired preoperative positioning devices of the broken bone segments. Hence, not only the images of all broken bone segments, but also the images of the positioning devices mounted on the broken bone segments are included in the said medical image information. Due to the different relationship between positioning balls of the positioning indicator included in each preoperative positioning device, each broken bone segment is corresponding to the three-dimensional image information of the matched positioning balls whose coordinates are different from each other.

According to the present invention, after obtaining the above medical image information, a pretreatment is performed thereon. According to CT-thresholds of bones, information of the bones and data information of the positioning balls in the preoperative positioning device are respectively extracted. The positioning ball is a stereoscopic ball. The data information of the positioning ball refers to the data of all points of which the ball is consisted. The ball center coordinates is spatial coordinates of the ball center of the stereoscopic ball calculated depending on these data. Then, the obtained information is subjected to noise reduction, filtering and other treatments to enhance information clearness. The pretreated information also includes complete information of all broken bone segments and the corresponding preoperative positioning devices.

According to the present invention, each broken bone segment and the preoperative positioning device mounted on this broken bone segment are considered as a group, and the obtained information is divided into several groups. It is thus obtained, in each case, the bone information of each broken bone which includes information of the preoperative positioning device. For example, in a case where the patient's humerus breaks into three segments, the three broken bone segments are respectively marked as a, b, c. Here, each broken bone segment, i.e., the segment a, the segment b, and the segment c have been respectively provided with a preoperative positioning device, and the positioning balls included in the preoperative positioning devices mounted on the segment a, the segment b, and the segment c have different spatial distribution rules with each other. According to an embodiment of the present invention, each positioning indicator has four positioning balls, and the positional relation between every four balls is fixed or is a fixed positional relation of three-dimensional coordinates. Particularly important is that the spatially relative positions of the ball centers in one group of positioning balls are different from that of the ball centers in another group of positioning balls. Hence, by identifying the ball center coordinates of the positioning balls in a positioning device, different positioning devices or positioning devices mounted on different broken bone segments can be differentiated and determined.

According to the present invention, groups of information of the broken bones and of the positioning devices obtained after the above division are respectively analyzed and calculated, obtaining ball center coordinates of the positioning balls included in each group. Each group of information includes the coordinate information of the four ball centers. After determining the information of the ball center coordinates, the corresponding relationship between the positioning indicator in the preoperative positioning device and the broken bone segment is determined according to the distribution rule of ball center coordinates of the positioning balls in three-dimensional space. In other words, it is obtained the matching relation or pairing relation between the each broken bone segment and the positioning indicator in the preoperative positioning device mounted thereon. It can be thus determined the one-to-one relationship between the each broken bone segment and the positioning indicator in the respective preoperative positioning device, for example, the matching relation between the broken bone segment a and the positioning indicator m in the respective preoperative positioning device. Then, the positional relation between the broken bone segment and the positioning indicator in the preoperative positioning device is calculated according to the information of the divided bone. For example, the positional relation between the broken bone segment a and the positioning indicator m in the preoperative positioning device is obtained. This positional relation includes not only the distance of the broken bone segment a with respect to the positioning indicator m or more exactly with respect to the ball center of each positioning ball, but also the pose of the broken bone segment.

Assuming that set A denotes the scanning information of the broken bone a based on the CT-coordinate system, any point on the broken bone a belongs to the set A. The broken bone a and the preoperative indicator group m are obtained in the same CT-scanning, so that the ball center coordinates of indicating balls in the preoperative indicator group m are all based on the CT-coordinate system. A preoperative indicator coordinate system is established on the preoperative indicator group m, following which a transformation relation between the preoperative indicator coordinate system and the CT-coordinate system, i.e. a rotation matrix R1 and a translation matrix T1, can be calculated based on the four ball center coordinates of the preoperative indicator group m. Hence, the scanning information of broken bone a in the preoperative indicator coordinate system, i.e. the positional relation between the broken bone a and the preoperative indicator group m, can be obtained via $A_{preoperative}$=F1 (A, R, T1), wherein $A_{preoperative}$ represents a set of scanning information of the broken bone a in the preoperative indicator coordinate system, and F1 represents a mapping relationship of coordinate transformation. In the same way, the positional relation between other broken bone segments and the respective preoperative indicator group can be calculated.

The preoperative positioning device may be replaced with an intraoperative positioning device after the relation between the above broken bone segments and the respective positioning indicators. Here, the connection between the positioning seat and the steel needles in the external fixator remains unchanged after the removal of the mounted preoperative positioning device.

According to the present invention, the position, distribution rule and etc. of the four positioning balls in the positioning indicator of the preoperative positioning device are completely as same as that of the four positioning balls in the positioning indicator of the intraoperative positioning device. The difference between the two groups of positioning balls only lies in the material. The positioning balls in the preoperative positioning device are metal balls, while the positioning balls in the intraoperative positioning device are non-metallic, for example, plastic balls coated with an infrared reflection material on their outer surface. The arrangement of such a distinction is for tracking and determining the positions of positioning balls using an infrared tracking apparatus during the surgery in accordance with the surgery navigation method of the present invention. It is thus avoided to use any radiation apparatus to determine the pose and position of the broken bones, avoiding the radiation damage to patients and medical staff.

Furthermore, in the surgery navigation method according to the present invention, the positioning support rod in the preoperative positioning device has a smaller length, while the positioning support rod in the intraoperative positioning device has a greater length. According to the present invention, the length ratio between the preoperative positioning support rod and the intraoperative positioning support rod is for example about 1:5. The relatively short positioning support rod in the preoperative positioning device enables the positioning indicator in the preoperative positioning device to come as close as possible to the skin of the patient's injured limb and to the broken bone segments. By this way, when performing the CT-scanning, interference or influence of the external fixator on the medical imaging can be maximally reduced. According to the present invention, it is better to attach the positioning seat in the preoperative positioning device on the patient's skin. During the surgery, the position of the positioning indicator is determined using an infrared tracking apparatus that is harmless to both of the doctor and the patient, it is thus, on one hand, required to sufficiently expose the positioning indicator in the area which can be directly irradiated by infrared light, in order to prevent the infrared light from being blocked or interfered by the external fixator; and, on the other hand, required to provide a sufficient surgical space for the doctor to perform a closed reduction surgery. Hence, according to the present invention, by increasing the length of the intraoperative positioning support rod, the intraoperative positioning indicator can be raised as high as possible up to a position which cannot be affected by the external fixator and which can provide a sufficient space for the doctor.

According to the present invention, the preoperative and intraoperative devices use the same positioning seat, and the positioning seat maintaining in a fixed connection to the steel needles after being mounted to the steel needle in the external fixator. Meanwhile, the spatial positional relation, distribution rule and etc. of the four positioning balls in the preoperative and intraoperative devices are completely the same. Hence, the positioning balls in the preoperative and intraoperative positioning indicators are changed only in the distance related to the respective broken bone segments, other corresponding relations thereof remaining unchanged. That is to say, if a coordinate system is established respectively based on the preoperative and the intraoperative positioning device, there is only a translational relationship between the two coordinate systems. It follows that as for the positioning indicators or the positioning balls, in addition to the difference caused by the different length of the preoperative and intraoperative positioning support rods, the deviation between the preoperative position and the intraoperative position is merely the mechanical machining error of its components, i.e., the preoperative and intraoperative positioning support rods and the preoperative and intraoperative positioning indicators.

After replacement with the intraoperative positioning device, infrared ray is used to seek and track positioning balls, determining the data information and the respective distribution form or rule of the positioning balls. According to the information obtained by the infrared tracking, the information of ball center coordinates of each group of positioning balls is analyzed and calculated. The corresponding positioning indicator is further deduced. For example, the preoperative positioning indicator m' is determined via the calculation. According to the present invention, the relative positional relation between the four positioning balls is determined by means of the calculation of ball center coordinates. Four positioning balls forms a group, with the connection lines among ball centers of the four positioning balls building a three dimensional body. The pose of the three dimensional body is equivalent to the pose of a corresponding broken bone segment in the three dimensional space. In other words, the three-dimensional vector coordinates of the corresponding broken bone segment can be deduced by determining the three-dimensional coordinates of the four positioning balls and the distribution rule thereof.

The preoperative positioning indicator m and the intraoperative positioning indicator m' have the same correspondence, it can be thus deduced that the intraoperative positioning indicator m' is corresponding to the broken bone segment a.

Due to the same spatial distribution of the indicating balls in the preoperative and intraoperative indicators which are corresponding to each other and which only have a different length as for the indicator rod, there is only a translational relationship, i.e. a translation matrix T2, between the two coordinate systems which are respectively established based on the preoperative indicators and the intraoperative indicators. $A_{intraoperative}$ is calculated by $A_{intraoperative}$= F2 ($A_{preoperative}$, T2), wherein $A_{intraoperative}$ represents a set of scanning information of the broken bone a based on the intraoperative indicator coordinate system, and F2 represents the mapping relationship of coordinate transformation. Similarly, the spatial relationship between other broken bones and respective intraoperative indicators can be calculated. By identifying the indicating balls of each intraoperative indicator, the ball center coordinates of each indicating ball can be calculated. According to the ball center coordinates, the spatial distribution of the intraoperative indicators can be determined, thereby obtaining an indicator group to which the current intraoperative indicators are subordinate, and calculating the spatial pose of each intraoperative indicator group. According to the positional pose of each indicator group, a model of each broken bone is rendered and displayed in real time.

The obtained model of the above broken bones is then projected to a display device, for example a display screen or a head-mounted VR device, so as to guide the doctor to perform a closed reduction surgery to the broken bones.

The positioning device according to the present invention is for scanning fractures or broken bone parts by CT before the surgery, obtaining morphological image information of the fractures or the broken bones; tracking and collecting positional information of the positioning device via an infrared device during the surgery and matching with the morphological information of the fractures obtained before the surgery; finally providing a three-dimensional image information of the fracture contour for the doctor to guide he/she to accurately perform the closed reduction surgery.

Figure 2:
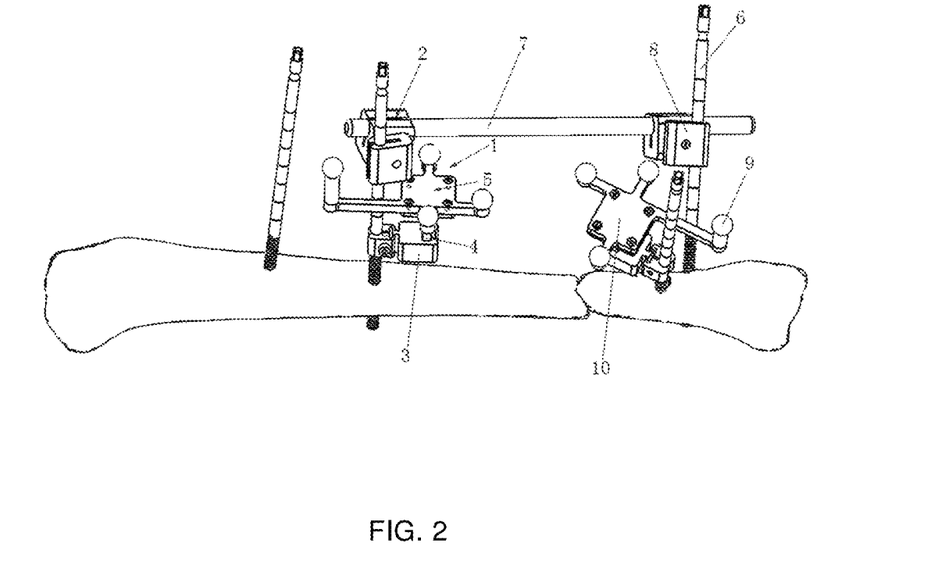
FIG. 2 is a schematic structural diagram of a positioning mechanism for fracture closed reduction used for a preoperative indicator according to an embodiment in the present invention.

FIG. 2 is a schematic structure diagram showing an embodiment of the positioning device according to the present invention. For clarity, the CT-apparatus for performing a preoperative scanning, the related apparatus for processing the scanning information and etc. are not shown in FIG. 2.

As shown in FIG. 2, the preoperative positioning device 1 for preoperative scanning includes a positioning seat 3, a preoperative positioning support rod 4 and a preoperative positioning indicator 5. As shown in FIG. 2, the preoperative positioning indicator 5 includes four preoperative positioning balls 9 and a preoperative support bracket 10 for supporting these preoperative positioning balls. According to the present invention, each broken bone segment is provided with one corresponding preoperative positioning indicator 5. Hence, according to the situation of different patients, it may be needed to provide different number of preoperative positioning indicators 5. For example, in the case of humerus fracture, if the patient's humerus breaks into three segments, the broken bone segments are marked as segment A, segment B, and segment C. According to the present invention, a preoperative positioning indicator 5 is respectively provided for each segment of the broken humerus. In the present example, it is needed to provide three preoperative positioning indicators 5. In order to differentiate each specific preoperative positioning indicator 5 which is corresponding to a certain specific broken bone segment and further clearly differentiating different broken bone segments in the next step of positioning the broken bone, the relative positions of the positioning balls 9 in each preoperative positioning indicator 5 are different from each other. For example, four preoperative positioning balls 9 are used in a preoperative positioning indicator 5 which are respectively marked as ball a, ball b, ball c, and ball d. Hence, the positioning balls in the preoperative positioning indicator 5 fixed on the broken bone segment A are ball a, ball b, ball c, and ball d. And the positioning balls in the preoperative positioning indicator 5 fixed on the broken bone segment B are ball a', ball b', ball c', and ball d'. According to the present invention, the spatial positional relation of the above ball a, ball b, ball c, and ball d is different from that of the ball a', ball b', ball c', and ball d'. For example, the horizontal distance between ball a and ball b is different from the horizontal distance between ball a' and ball b', and the distance between ball a and ball b in the vertical direction is also different from that between ball a' and ball b' in the vertical direction. In a word, every four balls is corresponding to one broken bone segment, and the positional relation between the balls or the distribution rule of the four balls is different from that of the other four balls. For this purpose, each broken bone segment is provided with a certain preoperative positioning indicator 5.

The external fixator 2 for affixing the fractures or broken bones includes a steel needle 6 and a connecting bar 7 connected to each steel needle 6. According to the present invention, the positioning seat 3 in the preoperative positioning device 1 is nearer to the fracture or broken bone, attached on the skin of the injured limb. The length of the intraoperative positioning support rod 4 is short such that the preoperative positioning indicator 5 supported by the preoperative positioning support rod on the positioning seat 3 is nearer to the skin surface of the injured limb. The purpose of placing the preoperative positioning device 1 as near as possible to the skin of the injured limb is to meet the requirements on scanning range and scanning density of the preoperative CT-scanning, so as to most possibly capture the position or image of the preoperative positioning indicator or positioning balls in the preoperative positioning device via the CT-apparatus. If the position, in which the preoperative positioning device is placed, is too high, far away from the skin, it may lead to a situation where the CT apparatus cannot fully capture the preoperative positioning indicator, and further lead to failure of positioning.

The external fixator 2 in FIG. 2 comprises steel needles 6 implanted in the fracture or broken bone segments and a connecting bar 7 for connecting the steel needles to each other so as to affix the broken bone segments to each other. In the present embodiment, the steel needles 6 and the connecting bar 7 are detachably connected to each other via a connection mechanism 8. Normally, in the first diagnosis of a patient, the number of steel needles to be implanted in each broken bone segment is determined based on the specific position of broken bone or fracture of the patient's injured limb as well as the state of fracture. Generally, it is required to provide at least one steel needle 6 on each broken bone segment. According to the position of the broken bones and the strength of the connecting bar 7, two or more steel needles 6 can be connected via one connecting bar 7. Having arranged the steel needles and selected the connecting bar 7, the selected steel needles 6 and connecting bar 7 are detachably connected to one another via the connection mechanism 8. Bone segments of the fracture or broken bone are thus temporarily affixed to one another, preventing a relative displacement of broken bone segments as moving the patient or in the patient's own movement.

Figure 3:
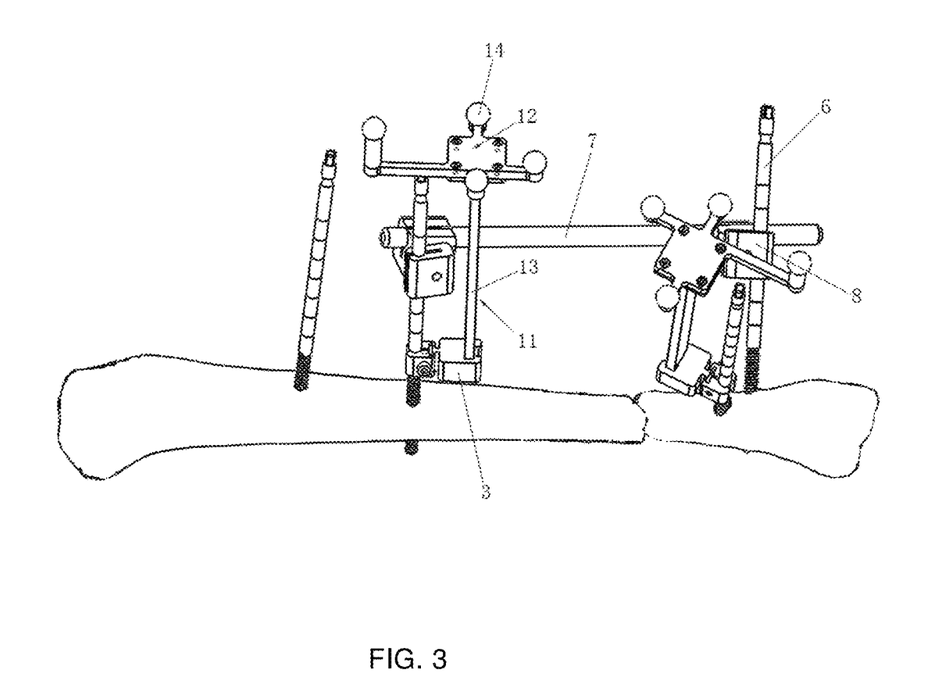
FIG. 3 is a schematic structural diagram of a positioning mechanism for fracture closed reduction used for an intraoperative indicator according to an embodiment in the present invention.

FIG. 3 schematically shows an intraoperative positioning device 11 according to the present invention. As shown, the intraoperative positioning device 11 comprises an intraoperative positioning indicator 12, an intraoperative positioning support rod 13 and a positioning seat 3. It can be seen from the figure that the length of the intraoperative positioning support rod 13 is greater than the length of the preoperative positioning support rod 4. According to an embodiment of the present invention, for example, the length ratio between the preoperative positioning support rod 4 and the intraoperative positioning support rod 13 is 1:5. The intraoperative positioning indicator 12 has the exactly same structure and shape as the preoperative positioning indicator 5. The difference therebetween lies in that the positioning balls 9 in the preoperative positioning indicator 5 are made of a metallic material, for example, aluminum, while intraoperative positioning balls in the intraoperative positioning indicator 12 are plastic balls coated with an infrared reflection layer. It can be seen from the figure that the intraoperative positioning indicator 12 in the intraoperative positioning device 11 is further from the fractures or broken bones, or is in a relatively high position. As performing a minimally invasive closed surgery, the doctor, on one hand, performs a closed reduction to the fractures or broken bones, which needs sufficient space for performing the surgery; on the other hand, uses an infrared tracking apparatus to track and capture the form, position and other information of the fractures during the surgery, in order to decrease radiation damage to the patient and medical staff in the present invention, which requires the positioning device to avoid the external fixator 2 arranged on the injured limb before the surgery, enabling the infrared tracking apparatus to detect the intraoperative positioning indicator 12 of the intraoperative positioning devices 11 during the surgery and capture its positional information. According to the present invention, for each broken bone segment or fracture segment, at least one intraoperative positioning device 11 according to the present invention is provided on the steel needle 6 implanted in the broken bone. It can be also seen from the figure that the positioning seat 3 for the intraoperative positioning device 11 is as same as the positioning seat 3 for the preoperative positioning device 1, i.e. their structures are completely the same.

According to the present invention, the preoperative positioning device 1 and the intraoperative positioning device 11 are respectively used before and during the closed reduction surgery, in order to accurately scan and determine form information of the fractures or broken bones before the surgery, and capture positioning information during the surgery so as to facilitate medical staff performing the closed reduction surgery. As preoperatively scanning and capturing medical images of the broken bones or fractures, the preoperative positioning device 1 according to the present invention is used to perform scanning and positioning. As intraoperatively performing the closed reduction surgery to the broken bones, the intraoperative positioning device 11 is used to track the intraoperative positioning indicator 12 in the intraoperative positioning device 11 via infrared tracking, then intraoperatively determining the position and form of the broken bones in real time via comparison with the information captured preoperatively, and displaying the broken-bone information to the doctor in the surgery, so as to guide the doctor to perform the surgery. Radiation damage to the patient, the doctor and the related medical staff during the surgery can be therefore prevented.

Figure 4:
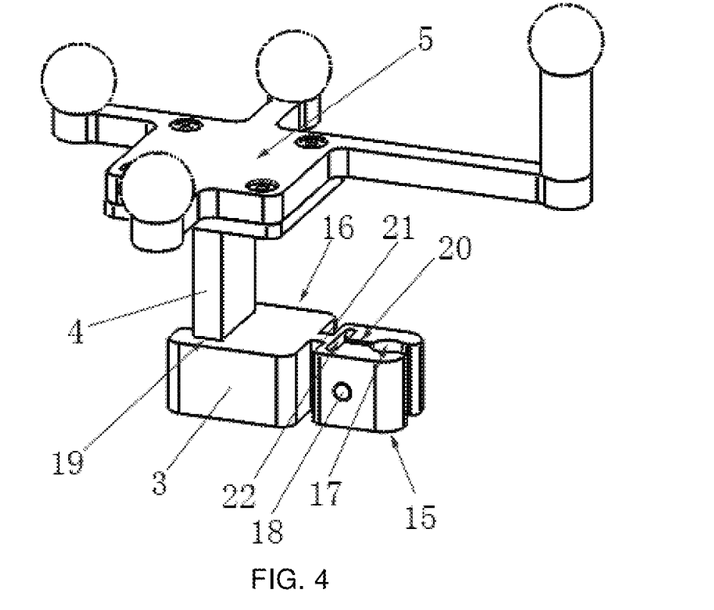
FIG. 4 is a schematic diagram of a preoperative positioning mechanism according to an embodiment in the present invention.
Figure 5:
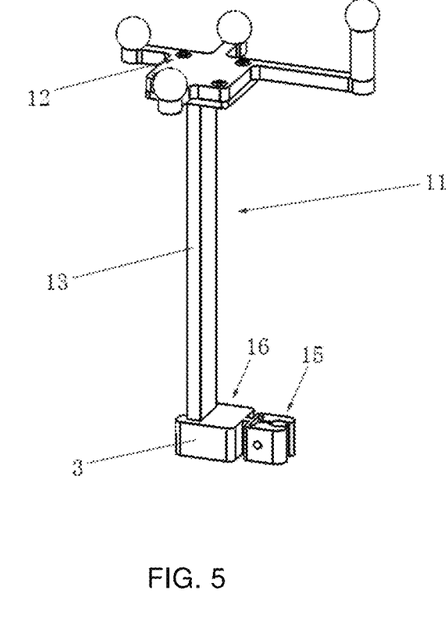
FIG. 5 is a schematic diagram of an intraoperative positioning mechanism according to an embodiment in the present invention.

FIG. 4 shows the preoperative positioning device 1 for use before the surgery according to the present invention. In combination with FIG. 4, it can be seen that the preoperative positioning device 1 according to the present invention is consisted of a positioning seat 3, a preoperative positioning indicator 5, and a preoperative positioning support rod 4. FIG. 5 shows the intraoperative positioning device 11 for use during the surgery according to the present invention. As shown in the figure, the intraoperative positioning device 11 according to the present invention is consisted of an intraoperative positioning indicator 12, an intraoperative positioning support rod 13, and a positioning seat 3. According to the present invention, the preoperative positioning support rod 4 in the preoperative positioning device 1 for use before the surgery has a smaller length, preferably a length of 20 mm in the present embodiment, while the intraoperative positioning support rod 13 in the intraoperative positioning device 11 for use during the surgery has a larger length, preferably a length of 100 mm in the present embodiment. According to the present invention, the ratio of length between the both is 1:5. Whereby, the preoperative positioning device 1 may ensure the positioning seat 3 to come as close as possible to the skin of the patient's injured limb, and the preoperative positioning indicator 5 is closer to the positioning seat 3, such that the CT-apparatus may fully scan the preoperative positioning indicator 5, obtaining complete information of the preoperative positioning device 1 and the form of the fracture or broken bone fixedly connected thereto. The intraoperative positioning support rod 13 in the intraoperative positioning device 11 for use during the surgery is relatively long, which may ensure the intraoperative positioning indicator 12 to stay as far as possible away from the external fixator 2 or avoid the external fixator 2, such that the intraoperative positioning indicator can be tracked or detected successfully by the infrared tracking apparatus without being shielded. Besides, in the embodiments shown in FIG. 4 and FIG. 5, the structures and compositions of the positioning seat 3 in the preoperative positioning device 1 and the intraoperative positioning device 11 are completely the same. According to the present invention, the difference between the preoperative positioning device 1 and the intraoperative positioning device 11 lies in the length of the positioning support rod and the material of positioning balls. The positioning balls in the preoperative positioning indicator 5 used for preoperative scanning are made of a metallic material, for example, aluminum or other materials for ease of identification by CT-scanning. The positioning balls in the intraoperative positioning indicator 12 used for intraoperative tracking are made of a plastic material coated with an infrared reflection material on the surface. In the present embodiment, four positioning balls are used in each group, which are not co-planar and three of which are not co-linear. More important in the present invention is that the preoperative positioning indicator 5 used for the preoperative positioning device 1 has completely the same amount and relative spatial position or spatial distribution rule of positioning balls as the intraoperative positioning device 11. The preoperative positioning balls are as same as the intraoperative positioning balls, i.e. they have the same amount, distribution rule, and relative spatial position in each case, so that, based on the positioning balls, the broken bone segments corresponding to the positioning balls, and further the spatial positions and poses of the broken bone segments can be determined in the following intraoperative positioning navigation.

According to the present invention, the preoperative positioning support rod 4 or the intraoperative positioning support rod 13 is fixed or detachably connected to the preoperative positioning indicator 5 or the intraoperative positioning indicator 12. As mounting or replacing the positioning indicator, the indicator bar is normally mounted or detached together with the positioning indictor. But, in another embodiment of the present invention, it is also possible to provide an independent preoperative positioning support rod 4 or intraoperative positioning support rod 13, and then mounting the corresponding preoperative positioning indicator 5 or intraoperative positioning indicator 12 on the preoperative positioning support rod 4 or intraoperative positioning support rod 13.

In the actual practice, after affixing the external fixator 2 on the patient's broken bones, the positioning seats 3 are affixed on the steel needle 6 of the external fixator 2 and coming as close as possible to the patient's skin. After capturing the form information of the preoperative positioning device 1 and the related broken bones by CT-scanning, the preoperative positioning device 1 is disassembled, i.e., removing the preoperative positioning indicator 5 and the preoperative positioning support rod 4, only remaining the positioning seat 3 on the steel needle 6. Here, in comparison with the external fixator 2, the positioning seat 3 neither brings any additional uncomfortableness or inconvenience to the patient, nor causes any harm to the patient due to its small dimension and skin-tight contact with the patient's skin. Nor does it bring any influence to the transportation of patient or possible activities of the patient. The positional relationship between the positioning seat 3 and the steel needle 6 maintains unchanged in the state where information is captured by CT-scanning, so that the positioning seat 3 keeps serving as the positioning seat in the intraoperative positioning device 11 during the following closed reduction surgery of the broken bones. In this way, the position of the positioning seat 3 with respect to the steel needle 6 is consistent during the preoperative scanning and the intraoperative tracking, such that the position information of the broken bones can be accurately ensured to be consistent before and during the surgery. Exact position, pose and other information of the broken bones can be provided to the doctor who is performing the surgery.

According to the present invention, a combination of preoperative positioning support rod 4 and preoperative positioning indicator 5 is used before the surgery, and another combination of intraoperative positioning support rod 13 and intraoperative positioning indicator 12 is used during the surgery. In the two combinations of support rods and positioning indicators, on one hand, the rods have different length; and on the other hand, the positioning balls are made of different material, but the preoperative and intraoperative positioning balls in the two sets of positioning devices have the completely same relative positional relation in the space. Making the positioning balls of different material is intended to adapt for different scanning or tracking apparatuses. According to the present invention, it is particularly important that the positioning balls in the two sets of positioning devices before and during the surgery have the completely same relative positional relationship in the space. Meanwhile, the relative positional relations of positioning balls in the space are completely different from each other in different groups. In other words, for each broken bone segment, a positioning indicator with a different structure is provided. In this way, it can be clearly and accurately determined in the following information processing which group of positioning balls for preoperative scanning matches up with which group of positioning balls for intraoperative tracking, so as to mark the identical broken bone segment. Having determined the preoperative and intraoperative positioning devices, it can be determined which group of intraoperative positioning balls is corresponding to which broken bone segment, because the positioning bracket 3 is affixed on the corresponding broken bone segment or bone piece via steel needle 6. Hence, the positions of positioning balls can be determined by tracking the positioning balls during the surgery. In the three-dimensional coordinate system, the spatial position and pose of the corresponding broken bone or broken bone piece during the surgery can be thus determined by adding the length differential between the preoperative positioning support rod 4 and the intraoperative positioning support rod 13.

According to the present invention, the use of different positioning indicators and positioning support rods before and during the surgery may avoid using CT or X-ray scanning to determine the position of the broken bones. The spatial three-dimensional coordinates and pose of the corresponding broken bone or broken bone piece can be thus deduced via positions of the positioning balls. According to the present invention, the positioning balls are tracked via an infrared apparatus during the surgery, such that the patient and medical staff who are performing the surgery are not exposed to any radiation, preventing the in-situ persons in the surgery from being subjected to any radiation damage. Furthermore, the relative position or connection relationship of the preoperative and intraoperative positioning seat 3 with respect to the respective broken bone or broken bone piece is consistent, so that there is no image shift. At this time, even if there is a slight deviation between the locations of the broken bone positioned before and during the surgery, this deviation is only result from the manufacturing tolerance at the connection between the different positioning support rods and the positioning seat. However, the machining error of mechanical components is negligible in comparison with the position deviation caused by painting a mark on the patient's skin and then adhering an indicator on the human body in the prior art.

Referring to FIGS. 4 and 5, the positioning seat 3 of the preoperative positioning device 1 according to the present invention is consisted of two portions: a portion for connection to the steel needle 6, called as steel needle holder 15 in the present invention; and a portion for supporting and affixing the preoperative positioning support rod 4 or the intraoperative positioning support rod 13, called as positioning support rod holder 16 in the present invention. As shown, in the present embodiment, the steel needle holder 15 is rigidly connected to the positioning support rod holder 16. The purpose of the present invention can be also achieved by rigidly connecting them in other manners.

In the present embodiment, the steel needle holder 15 is designed as an elastic clip-shaped structure which is opened at one end, elastically connected at the other side. The steel needle holder 15 which is designed as an elastic clip is consisted of two portions: a portion for connection and fixation to the steel needle 6 and a clamping portion for fastening the above portion for connection and fixation.

In an embodiment of the present invention, an open notch 19 is provided at one end of the steel needle holder 15, and two opposing half-rounded grooves 17 are respectively provided in the direction extending from the open notch 19 towards the interior of the steel needle holder 15, which are moved towards each other and closed during the installation, so as to clamp the steel needle holder 15 on the steel needle 6. The steel needle holder 15 is also provided with a screw 18 for affixing the steel needle holder 15 to the steel needle 6 by twisting the screw 18 after mounting the steel needle holder 15 on the steel needle 6, so as to keep the steel needle holder 15 fixed with respect to the steel needle 6 during the following preoperative scanning, the intraoperative tracking, and the duration between the preoperative and intraoperative periods. This may contribute to the consistency of positioning information before and during the surgery. Certainly, the fixed relative positions of the both can be also achieved only by clamping the steel needle holder 15 on the steel needle 6 via its own elasticity. However, for installation and firm fixation, the use of an exclusive screw 18 is more reliable. In the present embodiment, two opposing protrusions 20 are provided behind the two half-rounded grooves 17 in the direction extending from the edge of notch 19 on the steel needle holder 15 to the interior of the steel needle holder 15. The screw 18 is provided on the two protrusions 20, running through one of the two protrusions and entering the other one. In the longitudinal direction extending towards the interior of the steel needle holder 15, a connection piece 21 is provided behind the protrusions 20. The connection piece 21 per se is elastically deformable such that the two portions—the two half-rounded grooves 17 and the two protrusions 20 which form the steel needle holder 15, may approach to or separate from each other.

As a variation, the steel needle holder 15 may be a semi-closed ring. That is to say, the notch 19 in the previous embodiment is closed here, behind which there is also provided two protrusions which are separated from each other, remaining a gap between them, in order to accommodate the screw 18. Before mounting the external fixator 2, the steel needle holder 15 of such a structure is mounted on a given steel needle 6 and then affixed on the steel needle 6 via a fastening mechanism, remaining them in fixed relative positions. In a word, according to the concept of the present invention, the steel needle holder 15 may be a semi-closed ring, may have an open notch 19, may have a screw-fastening mechanism, and may be clamped on the steel needle 6 only by the aid of its own elasticity. As the above embodiment mentioned, the structure, in which the open-type steel needle holder 15 matches up with a screw 18, can be conveniently and simply mounted and affixed in a safe and reliable manner.

It can be known from FIGS. 4 and 5, in the present embodiment, the steel needle holder 15 is designed as two halves in substantially bilateral symmetry which are connected to each other via a narrow connecting piece 21 such that the left and right halves can be elastically moved with respect to each other. The relatively spaced arrangement of the left and right halves forms the notch 19 of the steel needle holder 15. Opposing protrusions 20 are provided in the middle of the two halves, with a space is remained between the two protrusions 20. By this way, a fixing member, the screw 18, can be provided at the protrusions 20 such that the two protrusions 20 can be brought into movement toward each other or away from each other by rotating the screw 18. The steel needle holder 15 can be thereby fastened on the steel needle 6 or loosed from the steel needle 6. The connection piece 21 for elastically connecting the two halves to each other is situated behind the protrusions 20. In order to enhance elasticity between the two halves, there is further provided a through groove 22 between the protrusion 20 and the connection piece 21.

In combination with FIGS. 4 and 5, it can be known that a positioning support rod seat 16 is in back-to-back connection to the steel needle holder 15 in the positioning seat 3. The positioning support rod seat 16 is for supporting and fixing the preoperative positioning support rod 4 or the intraoperative positioning support rod 13. In the present embodiment, the positioning support rod seat 16 is provided with a through groove 22 into which the preoperative positioning support rod 4 or the intraoperative positioning support rod 13 can be inserted. On the other side which is not shown in the figures, a screw is provided on a groove edge of the through groove 19. By tightening the screw, the preoperative positioning support rod 4 or the intraoperative positioning support rod 13 can be affixed and connected to the positioning support rod seat 16 in a fixed relative position. Certainly, by loosening the screw, the preoperative positioning support rod 4 or the intraoperative positioning support rod 13 is removed from the through groove 22, i.e. detaching the preoperative positioning support rod 4 or the intraoperative positioning support rod 13 from the positioning seat 3 together with the preoperative positioning indicator 5. It is significant for accomplishment of the purpose in the present invention, i.e. providing accurate fracture form information for medical staff which is performing the surgery, while reducing the radiation to the patent and medical staff. By means of such a structure, the installation and replacement of the preoperative positioning support rod 4 or the intraoperative positioning support rod 13 used for preoperative scanning and positioning and for intraoperative tracking and positioning can be simply and conveniently accomplished. Certainly, in order to achieve the purpose of the present invention, the through groove on the steel needle holder 15 of the positioning seat 3 may be rectangular, circular, hexagonal, or of other appropriate shapes. Correspondingly, the cross section for affixing the preoperative positioning support rod 4 or the intraoperative positioning support rod 13 may also has a shape of rectangle, circle, hexagon, or other appropriate shapes.

Figure 6:
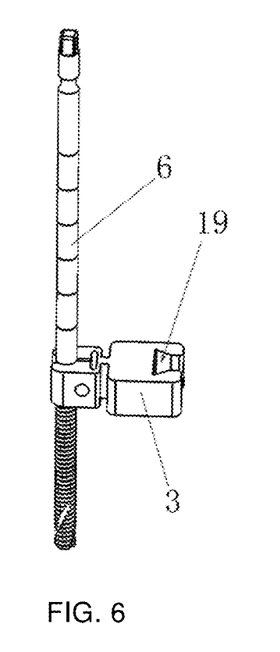
FIG. 6 is a schematic diagram of connection between an indicator holder and a steel needle according to an embodiment in the present application.
Figure 7:
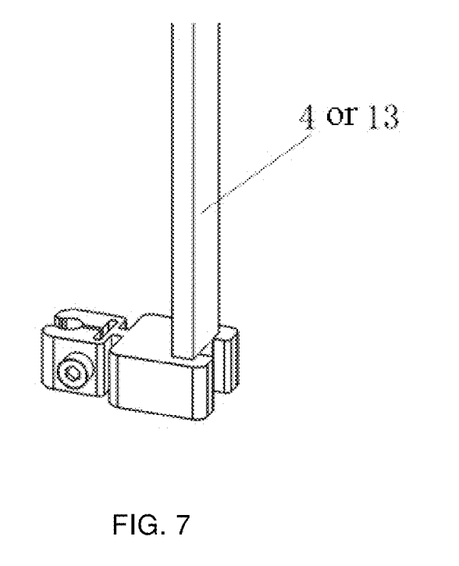
FIG. 7 is a schematic diagram of connection on another end of the indicator holder according to an embodiment in the present invention.

FIGS. 6 and 7 show a preferable embodiment of the through groove on the steel needle holder 15 of the positioning seat 3 according to the present invention. In such an embodiment, the fixation of the preoperative positioning support rod 4 or the intraoperative positioning support rod 13 can be achieved by matching a dovetail-shaped through groove with a trapezoidal cross section of the preoperative positioning support rod 4 or of the intraoperative positioning support rod 13. In the present embodiment, a bead screw is provided on the bottom of the dovetail groove. As inserting the preoperative positioning support rod 4 or the intraoperative positioning support rod 13 into the dovetail groove, the preoperative positioning support rod 4 or intraoperative positioning support rod 13 having a trapezoidal cross section can abut against either of walls of the dovetail groove by being pushed via the bead screw, such that the positional consistency is guaranteed in the replacement of the preoperative positioning support rod 4 or the intraoperative positioning support rod 13 and thereby enhancing the accuracy of positioning.

According to the present invention, the preoperative positioning device 1 and the intraoperative positioning device 11 belong to a group, and different broken bones are corresponding to different groups. According to the present invention, the positioning balls in the positioning indicators used for different broken bone segments are different from each other. That is to say, according to the present invention, the positioning balls for preoperative scanning and the positioning balls for intraoperative tracking, which are corresponding to one broken bone segment, are completely the same in positional relationship in the three-dimensional space. But, the positioning balls which are corresponding to different broken bone segments are completely different from each other in positional relationship in the three-dimensional space. Thus, the broken bone segment corresponding to the positioning balls can be determined during the surgery according to the distribution rule of the positioning balls obtained by tracking, and further determining the coordinates and pose of the broken bone segment.

Figure 8:
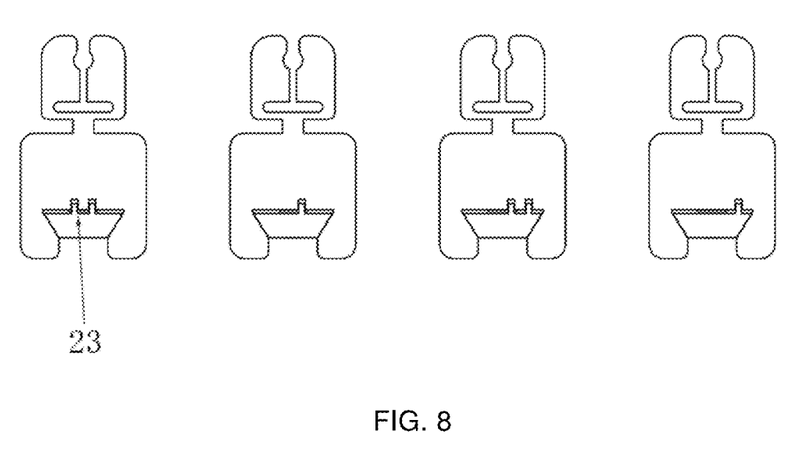
FIG. 8 is a schematic structural diagram of the misplug-proof structure according to an embodiment of the present invention.

In order to ensure accurately paired use of the preoperative positioning support rod 4 or intraoperative positioning support rod 13 and further high accurate positioning, it is provided a misplug-proof device in the embodiment shown in FIG. 8. As shown in FIG. 8, a different number of recesses are provided in different positions on the bottom of the dovetail groove in this embodiment. As shown, according to this embodiment, one and two recesses can be set at the bottom of the dovetail groove, and the recesses can be set at one side of the dovetail groove or in the middle. The number of recesses shall be selected on the premise of convenient installation and disassembly. Certainly, the recesses shown in the figure may either be recesses with a rectangular cross section, or recesses with a triangular cross section or arched cross section. Here, the recesses merely function to quickly differentiate from each other, instead of positioning or spacing. Accordingly, the preoperative positioning support rod 4 or the intraoperative positioning support rod 13 is also provided with a corresponding number of protrusions or flanges in corresponding positions on the corresponding side. In this way, in the actual use, when the protrusions or flanges are not matched to the recesses, the preoperative positioning support rod 4 or the intraoperative positioning support rod 13 cannot be inserted in the through groove of the steel needle holder 15 of the positioning seat 3. This may absolutely avoid disordered and staggered installation of different preoperative positioning support rods 4 or intraoperative positioning support rods 13 to different positioning seats 3, ensuring stable and consistent positioning accuracy. According to the concept of the present invention, a set of positioning device is corresponding to a broken bone segment. During the intraoperative tracking and positioning, the broken bone segment is determined by identifying the positioning device, and on which basis, the coordinates and pose the broken bone segment is deduced.

Figure 9:
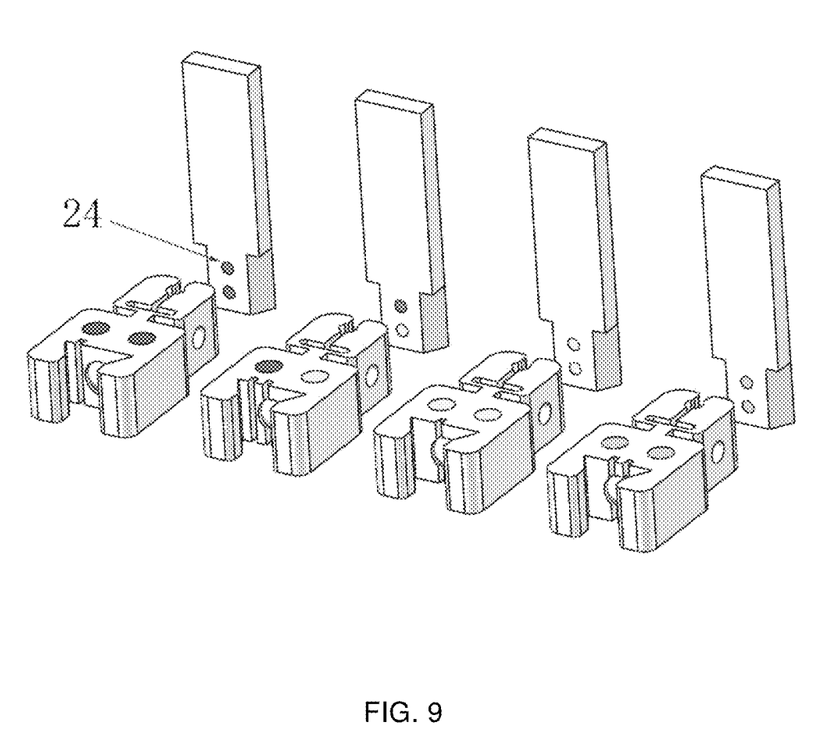
FIG. 9 is a schematic structural diagram for assembling the indicator structure according to an embodiment of the present invention.

In the embodiment shown in FIG. 9, different numbers, different colors and different shapes of indicators are respectively provided on a surface of the positioning seat 3 for positioning support rod seat 16 and on an end of the corresponding preoperative positioning support rod 4 or intraoperative positioning support rod 13. In the embodiment shown in the figure, two circles are provided in each case for characterization, in which different colors are filled. In the actual operation, guided by the indicators, the determination of paired positioning seats 3 and the fixation of preoperative positioning support rods 4 or intraoperative positioning support rods 13 can be simply and quickly achieved.

Figure 10:
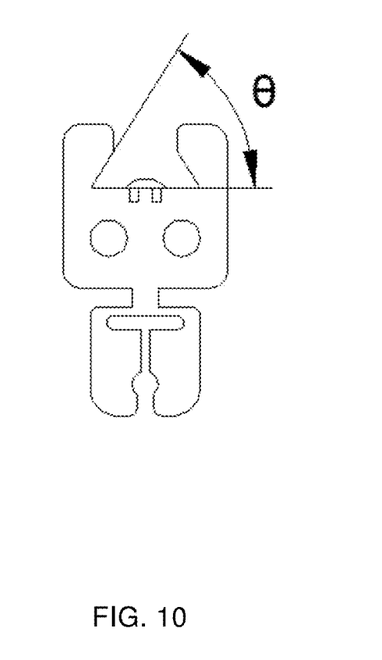
FIG. 10 is a schematic diagram of the angle of the dovetail groove according to an embodiment of the present invention.

FIG. 10 shows an embodiment of the dovetail groove for mounting the preoperative positioning support rod 4 and intraoperative positioning support rod 13 according to the present invention, wherein two opposing walls in the dovetail groove have an angle θ of 30°-80° with respect to the dovetail groove's bottom, which can achieve the purpose of keeping the positioning error between the preoperative positioning support rod 4 or intraoperative positioning support rod 13 and the positioning seat 3 very small, ensuring the positioning seat 3 to well clamp and support the preoperative positioning support rod 4 or intraoperative positioning support rod 13, and keeping the indicator rod standing firmly without swing or sway in the present invention. According to another embodiment of the present invention, the two opposing walls in the dovetail groove have an angle θ of 60° with respect to the bottom of the dovetail groove.

As performing a closed reduction surgery to each patient with fracture, it is firstly required to mount the positioning seat 3 according to the present invention on the given steel needle 6 and ensuring each broken bone or fracture to have at least one positioning seat 3. Then, a corresponding preoperative positioning support rod 4 is inserted in the positioning seat 3. At this time, the preoperative positioning indictor 5 has mounted and affixed on the preoperative positioning support rod 4. Having performed a CT-scanning to the injured limb and captured medical image information, the preoperative positioning support rod 4 is removed together with the preoperative positioning indicator 5. Now, the patient can be moved to a sickroom for rest. The positioning seat 3 mounted on the steel needle 6 does not interfere with patient's daily life. When the closed reduction surgery is needed to be performed, the intraoperative positioning support rod 13 corresponding to the positioning seat 3 is inserted therein and affixed thereto by tightening the screw 18. In the next step, the external fixator 2 is loosened, that is, the connection mechanism 8 between connecting rod 7 and steel needle 6 is loosened, relieving the restriction of the connecting rod on the steel needle 6. The reduction operation is performed by using a visible fracture reduction system containing an infrared apparatus. Having finished the reduction, the external fixator 2 is affixed again, and the intraoperative positioning support rod 13 and positioning seat 3 are subsequently removed.

In conclusion, according to the concept of the present invention, the preoperative positioning system comprising the preoperative positioning device is adopted to meet the requirement on scanning range and scanning density of the preoperative CT-scanning, ensuring operability of the entire system. The use of intraoperative positioning device meets the tracking and identifying requirement of the infrared tracking system. In addition, either the preoperative indicator or the intraoperative indicator can be quickly detached after usage, without interfering patient's daily life.

The invention claimed is:

1. A method for positioning and navigation of a fracture closed reduction surgery, comprising:
    installing preoperative positioning devices on steel needles of an external fixator, performing CT-scanning to obtain image information of broken bones and the preoperative positioning devices;
    determining data information of broken bone segments and of positioning balls of the preoperative positioning devices;
    taking a broken bone segment and a preoperative positioning device as a group to divide the obtained data information into data groups, determining ball center coordinates of the positioning balls of the preoperative positioning device included in each data group, and determining a distribution rule of the positioning balls according to the ball center coordinates;
    determining a matching relation between each preoperative positioning device and the corresponding broken bone segment based on the ball center coordinates of the positioning balls;
    detaching preoperative positioning indicators and preoperative positioning support rods in the preoperative positioning devices from positioning seats, and installing intraoperative positioning indicators and intraoperative positioning support rods on the positioning seats;
    identifying positioning balls of the intraoperative positioning devices using infrared light tracking to determine ball center coordinates of the positioning balls in each intraoperative positioning device;
    determining spatial pose of the intraoperative positioning devices according to the ball center coordinates of each intraoperative positioning device, and determining spatial pose of each broken bone segment during the surgery according to a coordinate transformation relationship between the preoperative positioning devices and the intraoperative positioning devices; and
    rendering and displaying each broken bone segment model in real time.

2. The method for positioning and navigation of a fracture closed reduction surgery as claimed in claim 1, wherein one preoperative positioning device is provided at least on each broken bone segment.

3. The method for positioning and navigation of a fracture closed reduction surgery as claimed in claim 2, wherein the preoperative positioning devices comprise the preoperative positioning indicators and the preoperative positioning support rods, the intraoperative positioning devices comprise the intraoperative positioning indicators and the intraoperative positioning support rods, the preoperative positioning devices and the intraoperative positioning devices are configured to be mounted on the positioning seats, wherein the positioning indicators comprise the positioning balls; spatial positions of and a distance between the positioning balls for the preoperative positioning device and between the positioning balls for the intraoperative positioning device are the same; the positioning support rod of the preoperative positioning device has a length less than that of the intraoperative support rod.

4. The method for positioning and navigation of a fracture closed reduction surgery as claimed in claim 3, wherein the positioning balls of the preoperative positioning device are metallic balls, the positioning balls of the intraoperative positioning device are plastic balls coated with an infrared reflection layer on their surfaces.

5. The method for positioning and navigation of a fracture closed reduction surgery as claimed in claim 4, wherein the positioning balls which are corresponding to each other in the preoperative and intraoperative positioning devices have the same spatial position and distribution rule, and respectively have a respective Z-coordinate in the same three-dimensional coordinate system.

6. A positioning device for fracture closed reduction, comprising: a positioning seat (3), a positioning indicator, wherein further comprising a preoperative positioning support rod (4) or a intraoperative positioning support rod (13), the preoperative positioning support rod (4) or intraoperative positioning support rod (13) being connected to the positioning indicator at one end, and detachably affixed and connected to the positioning seat (3) at an other end, wherein the preoperative positioning support rod (4) has a length less than that of the intraoperative positioning support rod (13);
wherein the positioning seat (3) comprises a steel needle holder (15) and a positioning support rod seat (16), the steel needle holder (15) being rigidly connected to the positioning support rod seat (16); and
the steel needle holder (15) comprises a notch (19) disposed on one end, behind the notch two half-rounded grooves (17) that face each other are provided in the direction extending from the notch(19) towards an interior of the steel needle holder (15), behind the two half-rounded grooves (17) there is provided two opposing protrusions (20) on which a screw (18) is provided, and behind the two opposing protrusions (20) a connecting band (21) is provided to elastically connect the two opposing protrusions (20) to each other.

7. The positioning device for fracture closed reduction as claimed in claim 6, wherein the ratio of length between the preoperative positioning support rod (4) and the intraoperative positioning support rod (13) is 1:5.

8. The positioning device for fracture closed reduction as claimed in claim 6, wherein the positioning indicator is preoperative positioning indicator (5) or intraoperative positioning indicator (12), the preoperative positioning indicator (5) comprising preoperative positioning balls (9) which are metallic balls; the intraoperative positioning indicator (12) comprising intraoperative positioning balls (14) which are plastic balls coated with an infrared reflection layer on their surfaces; the ball centers in the preoperative positioning ball (9) and intraoperative positioning balls (14) have the same relative positions.

9. The positioning device for fracture closed reduction as claimed in claim 6, wherein the steel needle holder (15) comprises a circular through hole, behind which two protrusions (14) that face each other are provided in the direction extending towards an interior of the steel needle holder (15), a screw (13) is provided on the protrusions (14), and behind the protrusions (14) a connecting band (21) is provided to elastically connect the two protrusions (14) to each other.

10. The positioning device for fracture closed reduction as claimed in claim 9, wherein the positioning support rod seat (16) is provided with a through groove (22) which is provided with a screw on a lateral side.

11. The positioning device for fracture closed reduction as claimed in claim 6, wherein the positioning support rod seat (16) is provided with a through groove (22) which is provided with a screw on a lateral side.

12. The positioning device for fracture closed reduction as claimed in claim 11, wherein the through groove (22) has a rectangular, circular or hexangular cross section.

13. The positioning device for fracture closed reduction as claimed in claim 12, wherein the through groove (22) is provided with a misplug-proof groove (23) on the lateral side wall, and a misplug-proof protrusion (24) corresponding to the misplug-proof groove (23) on the lateral side wall of the through groove (17) is provided on a surface of the preoperative positioning support rod (4) or the intraoperative positioning support rod (13).

14. The positioning device for fracture closed reduction as claimed in claim 11, wherein the through groove (22) is a dovetail groove having an included angle θ of 30°-80°, and the cross section of the preoperative positioning support rod (4) or the intraoperative positioning support rod (13) is trapezoid which matches with a shape of the dovetail groove.

15. The positioning device for fracture closed reduction as claimed in claim 14, wherein the through groove (22) is provided with a misplug-proof groove (23) on the lateral side wall, and a misplug-proof protrusion (24) corresponding to the misplug-proof groove (23) on the lateral side wall of the through groove (17) is provided on a surface of the preoperative positioning support rod (4) or the intraoperative positioning support rod (13).

16. The positioning device for fracture closed reduction as claimed in claim 11, wherein the through groove (22) is provided with a misplug-proof groove (23) on the lateral side wall, and a misplug-proof protrusion (24) corresponding to the misplug-proof groove (23) on the lateral side wall of the through groove (17) is provided on a surface of the preoperative positioning support rod (4) or the intraoperative positioning support rod (13).

17. The positioning device for fracture closed reduction as claimed in claim 11, wherein indicator color spots which are corresponding to each other are respectively provided on the steel needle holder (15) and the preoperative positioning support rod (4) and/or intraoperative positioning support rod (13).

* * * * *